United States Patent [19]

Thunberg

[11] Patent Number: 5,159,110
[45] Date of Patent: Oct. 27, 1992

[54] PROCESS FOR RECOVERING N-METHYLIMINODIACETIC ACID FROM SODIUM SULFATE

[75] Inventor: Jon C. Thunberg, Milford, N.H.

[73] Assignee: W. R. Grace & Co.-Conn., New York, N.Y.

[21] Appl. No.: 782,847

[22] Filed: Oct. 24, 1991

Related U.S. Application Data

[63] Continuation-in-part of Ser. No. 701,285, May 16, 1991.

[51] Int. Cl.$^5$ ............................................. C07C 227/00
[52] U.S. Cl. ..................................................... 562/554
[58] Field of Search ......................................... 562/554

[56] References Cited

U.S. PATENT DOCUMENTS

| | | | |
|---|---|---|---|
| 3,463,812 | 8/1969 | Thunberg et al. | 260/534 |
| 3,510,515 | 5/1970 | Colburn et al. | 260/534 |
| 3,808,269 | 4/1974 | Bragdon et al. | 260/534 E |
| 3,852,344 | 12/1974 | Bragdon et al. | 260/534 E |
| 3,904,585 | 9/1975 | Thunberg et al. | 260/534 E |
| 3,932,501 | 1/1976 | Thurnberg et al. | 260/534 C |
| 3,947,496 | 3/1976 | Thunberg et al. | 260/534 R |
| 3,985,801 | 10/1976 | Thunberg et al. | 260/534 R |
| 4,299,978 | 11/1981 | Nakayasu et al. | 562/554 |
| 4,306,880 | 12/1981 | Garrett | 23/295 S |
| 4,691,054 | 9/1987 | Tosa et al. | 562/554 |
| 4,818,409 | 4/1989 | Puetter et al. | 210/638 |
| 4,986,976 | 1/1991 | Thunberg | 423/551 |
| 5,011,988 | 4/1991 | Thunberg | 562/554 |

FOREIGN PATENT DOCUMENTS

| | | |
|---|---|---|
| 0081063 | 10/1982 | European Pat. Off. |
| 1493723 | 9/1967 | France |
| 5313609 | 8/1972 | Japan |
| 5673620 | 11/1979 | Japan |
| 1472840 | 9/1975 | United Kingdom |

*Primary Examiner*—Michael L. Shippen
*Attorney, Agent, or Firm*—Kevin S. Lemack; William L. Baker

[57] ABSTRACT

N-methyliminodiacetic acid is separated from mixtures of N-methyliminodiacetic acid and sodium sulfate formed by acidification of solutions of its disodium salt with sulfuric acid. Thus the disodium salt is acidified with sulfuric acid to a pH of about 2 and concentrated by evaporating water so as to crystallize sodium sulfate. The sodium sulfate is separated, and the resulting mother liquor is cooled to precipitate N-methyliminodiacetic acid, which is then separated.

5 Claims, No Drawings

PROCESS FOR RECOVERING N-METHYLIMINODIACETIC ACID FROM SODIUM SULFATE

This is a Continuation-in-part of application Ser. No. 07/701,285, filed May 16, 1991.

BACKGROUND OF THE INVENTION

This invention is directed to a process for preparing N-methyliminodiacetic acid, and in particular, a process for recovering the same from solutions of its disodium salt.

In the prior art, amino acids such as glycine and B-alanine have been prepared by hydrolyzing the corresponding nitrile with an aqueous alkaline earth metal hydroxide to form an alkaline earth metal salt of the amino acid, and treating the alkaline earth metal salt with carbon dioxide to form the free amino acid, and recovering the amino acid.

Another method of producing such amino acids includes treatment with sulfuric acid to convert the intermediate sodium salt (such as sodium glycinate in the case of glycine) to the free amino acid. However, such a process results in the formation of sodium sulfate, which is difficult to separate from the free amino acid.

U.S. Pat. Nos. 3,904,585 and 3,947,496 to Thunberg et al., the disclosures of which are incorporated by reference, disclose a process for separating glycine or B-alanine from such sodium sulfate solutions by fractional crystallization. Specifically, in the starting aqueous solution of sodium sulfate and the amino acid, which has a temperature above 33° C., a pH of 4.5–8.5, a mole ratio of amino acid to sodium sulfate of 1–5:1, and containing at least 5% of the amino acid, water is evaporated at a temperature of from 60° C. or 70° C. to about the normal boiling point in order to form a first slurry which is a mixture of precipitated sodium sulfate and a first mother liquor. The temperature is such that the precipitation of the amino acid is prevented. Upon separation of the precipitated sodium sulfate, the mother liquor is cooled to a temperature effective for precipitating the amino acid. The amino acid is separated and recovered, and the process is repeated.

U.S. Pat. No. 3,808,269 to Bragdon et al. discloses a similar process, except that iminodiacetic acid is separated from sodium sulfate solutions.

Methyliminodiacetic acid is of interest for photographic applications. In Chemical Abstracts 111(8):67804u, for example, it is disclosed that a bleaching solution for bleaching an exposed photographic material contains Fe(III) complex salts of organic acids including methyliminodiacetic acid. Similarly, in Chemical Abstracts 93(6):588196e, a bleaching solution comprised of $FeCl_3$, KBr and methyliminodiacetic acid, adjusted to a pH of 6.0 with $NH_3$, is disclosed. In Chemical Abstracts 77(4):24608v, the biodegradation of N-methyliminodiacetic acid in river water is disclosed.

Although other, perhaps more effective, chelating agents exist, N-methyliminodiacetic acid is biodegradable, thus making its use highly desirable in terms of environmental concerns. However, where N-methyliminodiacetic acid is formed from its disodium salt by acidification with sulfuric acid, separation of the acid from the resulting sodium sulfate solution is problematic. None of the foregoing patents suggests the application of fractional crystallization for the separation of N-methyliminodiacetic acid from such solutions.

SUMMARY OF THE INVENTION

The problems of the prior art have been solved by the instant invention, which provides a process for separating and recovering N-methyliminodiacetic acid ("MIDA") from sodium sulfate solutions by fractional crystallization, either batchwise or continuously.

DETAILED DESCRIPTION OF THE INVENTION

N-methyliminodiacetic acid can be formed from its disodium salt by acidification with sulfuric acid. The disodium salt can be formed by alkaline hydrolysis of N-methyliminodiacetonitrile ("MIDAN") by saponification with sodium hydroxide. The synthesis of MIDAN is described by Eschweiler, Annelen, 279, 41, of which the disclosure is incorporated herein by reference, as follows:

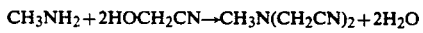

$$CH_3NH_2 + 2HOCH_2CN \rightarrow CH_3N(CH_2CN)_2 + 2H_2O$$

Indeed, analogous chemistry has been applied to the preparation of N-ethyliminodiacetonitrile, as described in J.A.C.S. 80, 5944 (1958), the disclosure of which is herein incorporated by reference, and to the preparation of 2-hydroxyethyliminodiacetonitrile, as described in U.S. Pat. No. 3,864,378, the disclosure of which is herein incorporated by reference.

Upon alkaline hydrolysis of the MIDAN, the resulting disodium salt solution has a pH of greater than about 11. In the preferred embodiment of the present invention, a solution of the disodium salt of MIDA at a temperature of about 80° C. is acidified with sulfuric acid to a pH of approximately 2 (about the isoelectric point of MIDA). The acidified solution is then concentrated to remove water and to simultaneously crystallize anhydrous sodium sulfate. The concentration step is carried out at a temperature sufficient to prevent the co-precipitation of MIDA. (The saturation temperature of MIDA will depend upon the original concentration of MIDA-$Na_2$ in the starting solution). The precipitated anhydrous sodium sulfate is separated from the hot slurry and the resulting first mother liquor is cooled to a temperature effective for precipitating N-methyliminodiacetic acid in a second mother liquor while avoiding the precipitation of anhydrous sodium sulfate or sodium sulfate decahydrate. Preferably the temperature to which the first mother liquor is cooled is just above the transition temperature (approximately 32.4° C.) of sodium sulfate/sodium sulfate decahydrate. A temperature of about 35° C. has been found to be suitable. The precipitated acid is separated and recovered from the second mother liquor, and the latter may then be recycled to an appropriate earlier stage in the process such as the concentration step, and the process repeated.

The aforementioned separations of the precipitated sodium sulfate and MIDA are preferably accomplished by centrifugation, although other forms of separation such as filtration or decantation could be used.

The concentration of MIDANa2 in the starting solution must be in a range so that upon acidification, sodium sulfate is not co crystallized. Those skilled in the art will also appreciate that the temperature at which the acid precipitates is a function of the original concentration of the disodium salt, and thus either can be adjusted accordingly. Preferably the MIDANa2 feedstock for the fractional crystallization is about a 30% MIDA-$Na_2$ solution.

In an additional embodiment, purge liquor from the fractional crystallization scheme can be cooled to a temperature low enough to precipitate, in the same mother liquor, both MIDA and sodium sulfate decahydrate. The resulting precipitate, which is a mixed wet cake of MIDA and sodium sulfate decahydrate (Glauber's salt), can be separated from its mother liquor by centrifugation, and recycled to an earlier point in the production process of MIDANa$_2$. Water can be added to the cake to form a pumpable stream. All or a portion of the mother liquor can be recycled to the MIDA/sodium sulfate decahydrate crystallizer to reduce the slurry density.

Appropriate seeding may be carried out to initiate or enhance the various crystallizations.

The instant invention will be better understood by referring to the following specific but non-limiting examples. It is understood that modifications can be made without departing from the spirit and scope of the present invention.

EXAMPLE 1

Fractional Crystallization 1000 grams of MIDANa$_2$ solution (approximately 41.2%) was added to a stainless steel beaker and 280 grams of H$_2$O was charged. Starting at ambient temperature, a total of 639.5 grams of 50% H$_2$SO$_4$ was added to lower the pH to 2.0. The temperature rose during the addition to about 65° C. With vigorous stirring and a gas burner, the solution was concentrated by boiling to 1114 grams. The resulting 80°-90° C. material was placed into a plastic 2 liter graduate. 200 ml. of crystals out of 720 ml. settled to the bottom. The material was then centrifuged hot (the centrifuge was heated with steam). 755.7 grams of liquor and 203.2 grams of sodium sulfate were recovered.

The recovered liquor was cooled to 35° C. and allowed to stir at 35° C. overnight. During this time, 114.6g of water was lost by evaporation, thereby providing a slurry weighing 641.1g the next morning. The slurry was centrifuged at 35° C. and washed with water. 441.6 grams of liquor, 113.6 grams of MIDA and 172.6 grams of washings were recovered.

EXAMPLE 2

Fractional Crystallization

The feedstock was a 31.9% solution of MIDANa$_2$. To a 2 liter graduated Pyrex beaker was added 1.00 kg of MIDANa$_2$ and sufficient water to give a 30% MIDANa$_2$ solution. To this was added liquor from a previous cycle. 93% H$_2$SO$_4$ was added to a pH of 2.0 while cooling to keep the temperature less than or equal to 60° C. This solution was boiled until the volume percent of settled crystals was approximately 20%. The centrifuge was heated with steam and then the hot slurry (greater than 80° C.) was separated. The Na$_2$SO$_4$ cake was not washed before being dried.

The hot liquor was cooled to 35° C., placed in a 35° C. water bath, and stirred overnight. The slurry formed was centrifuged in the previously warmed centrifuge. The MIDA crystals were washed with approximately 10 ml. of water. The liquor was recycled to the next crystallization, and the process was repeated for a total of 15 cycles. No deterioration of crystallinity was observed and no solids/liquids separation problems arose. The liquor from the 15th cycle was carried through one more cycle in which no fresh MIDANa$_2$ was added. No crystallization problems occurred in this cycle. The absence of crystallization problems suggests that additional cycles would increase yield. Table 1 reports the data obtained from the foregoing.

TABLE I

Summary of Data from Cyclic MIDA Fractional Crystallization Experiments

| Cycle No. | Materials Charged Gms | | | | Weights Gms | | | Weight Gms Before Cool Down |
|---|---|---|---|---|---|---|---|---|
| | MIDA No$_2$ | H$_2$O Added | 93% H$_2$SO$_4$ | Liquor & Wash | Before Boil-off | After Boil-off | % Boiled off | |
| 1 | 1000 | 383 | 186 | 0 | 1569 | 1251 | 20.3 | 1047 |
| 2 | 1000 | 383 | 298 | 903 | 2584 | 1964 | 24 | 1524 |
| 3 | 1000 | 383 | 233 | 936 | 2553 | 2029 | 20.5 | 1704 |
| 4 | 1000 | 383 | 267 | 1384 | 3034 | 2391 | 21.2 | 2006 |
| 5 | 1000 | 383 | 200 | 1475 | 3058 | 2458 | 19.6 | 2201 |
| 6 | 1000 | 383 | 279 | 1994 | 3656 | 2916 | 20.2 | 2414 |
| 7 | 1000 | 383 | 224 | 1652 | 3259 | 2578 | 21.1 | 2168 |
| 8 | 1000 | 383 | 423 | 1593 | 3399 | 2718 | 20.1 | 2311 |
| 9 | 1000 | 383 | 258 | 1683 | 3323 | 2425 | 27.0 | 1922 |
| 10 | 1000 | 383 | 235 | 1029 | 2647 | 2117 | 20.0 | 1787 |
| 11 | 1000 | 383 | 305 | 1340 | 3029 | 2324 | 23.3 | 1937 |
| 12 | 1000 | 383 | 224 | 657 | 2264 | 1754 | 22.5 | 1447 |
| 13 | 1000 | 383 | 250 | 1080 | 2713 | 2141 | 21.1 | 1793 |
| 14 | 1000 | 383 | 250 | 1240 | 2868 | 2224 | 22.5 | 1866 |
| 15 | 1000 | 383 | 278 | 1353 | 3014 | 2314 | 23.2 | 1907 |
| 16 | 1000 | 383 | 116 | 1220 | 1336 | 1051 | 21.4 | 860 |
| 17 | | | | | | | | |
| 18 | | | | | | | | |

| Cycle No. | Contained MIDA Charged | | Materials Recovered | | | | Gms of Contained MIDA | | Cumulative % Yield |
|---|---|---|---|---|---|---|---|---|---|
| | This Cycle | Cumulative | MIDA, gms | Na$_2$SO$_4$ gms | Liquid & Wash, gms | % A.I. | This Cycle | Cumulative | |
| 1 | 319 | 319 | 0 | 154 | 903 | | 0 | 0 | 0 |
| 2 | 319 | 638 | 398 | 344 | 9362 | 94.0 | 374 | 374 | 58.6 |
| 3 | 319 | 957 | 193 | 248 | 1384 | 87.9 | 169 | 543 | 56.7 |
| 4 | 319 | 1276 | 309 | 291 | 1475 | 95.7 | 296 | 839 | 65.8 |
| 5 | 319 | 1595 | 70 | 253 | 1994 | 98.6 | 69 | 908 | 56.9 |

TABLE I-continued
Summary of Data from Cyclic MIDA Fractional Crystallization Experiments

|   |     |      |      |      |      |      |     |      |      |
|---|-----|------|------|------|------|------|-----|------|------|
| 6 | 319 | 1914 | 466  | 347  | 1652 | 91.1 | 425 | 1333 | 69.6 |
| 7 | 319 | 2233 | 28   | 319  | 1593 | 79.0 | 226 | 1559 | 69.8 |
| 8 | 319 | 2552 | 342  | 299  | 1683 | 95.4 | 326 | 1885 | 73.9 |
| 9 | 319 | 2871 | 511  | 384  | 1029 | 82.9 | 424 | 2309 | 80.4 |
| 10| 319 | 3190 | 253  | 241  | 1340 | 84.6 | 214 | 2523 | 79.1 |
| 11| 319 | 3509 | 592  | 292  | 657  | 66.0 | 391 | 2914 | 83.0 |
| 12| 319 | 3828 | 228  | 225  | 1080 | 77.3 | 176 | 3090 | 80.7 |
| 13| 319 | 4147 | 315  | 240  | 1240 | 82.1 | 259 | 3349 | 80.8 |
| 14| 319 | 4466 | 309  | 265  | 1353 | 86.3 | 267 | 3616 | 81.0 |
| 15| 319 | 4785 | 342  | 341  | 1277 | 94.3 | 323 | 3939 | 82.3 |
| 16| 319 | 4785 | 122  | 139  | 649  | 80.2 | 98  | 4037 | 84.4 |
| 17|     |      | 4737 | 4382*|      |      |     |      |      |
| 18|     |      |      |      |      |      |     |      |      |

*MIDA in composite sample = 2.2%

What is claimed is:

1. A process for recovering N-methyliminodiacetic acid from solutions comprising disodium N-methyliminodiacetate and sodium sulfate, comprising:
   a. adjusting the pH of said solution to about 2 with sulfuric acid;
   b. concentrating the pH adjusted solution to remove water and form a first slurry comprising crystallized anhydrous sodium sulfate and a first mother liquor;
   c. separating the crystallized anhydrous sodium sulfate from said mother liquor;
   d. adjusting the temperature of said first mother liquor so as to form a second slurry comprising precipitated N-methyliminodiacetic acid and a second mother liquor; and
   e. separating the precipitated N-methyliminodiacetic acid from said second mother liquor.

2. A process according to claim 1, wherein said solution is concentrated by evaporating water.

3. A process according to claim 1, wherein the temperature of said first mother liquor is adjusted by lowering the temperature thereof to just above the transition temperature of sodium sulfate and sodium sulfate decahydrate.

4. A process according to claim 1, further comprising recycling said second mother liquor.

5. A process according to claim 1, further comprising cooling said second mother liquor to a temperature effective for forming a slurry comprising a mixture of precipitated N-methyliminodiacetic acid and sodium sulfate decahydrate in a third mother liquor, and separating the precipitated N-methyiminodiacetic acid and sodium sulfate decahydrate from said third mother liquor.

* * * * *